Figure 1:
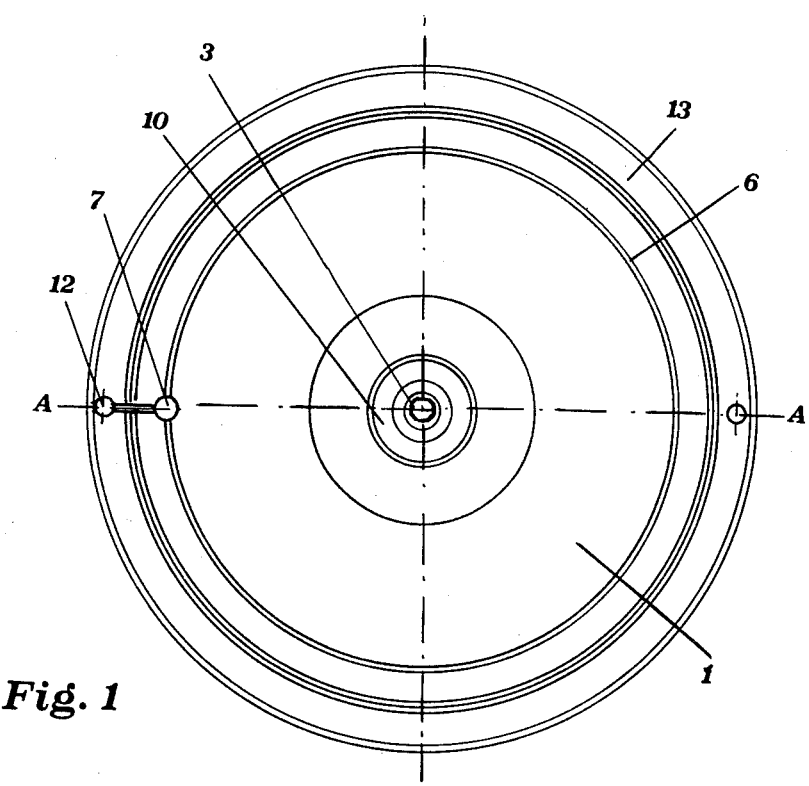

United States Patent [19]

Tropea

[11] 4,055,076

[45] Oct. 25, 1977

[54] CENTRIFUGAL GRANULOMETER

[76] Inventor: Michele Tropea, Viale A. Alagona, 27/H, Catania, Italy

[21] Appl. No.: 668,852

[22] Filed: Mar. 22, 1976

[30] Foreign Application Priority Data

Mar. 21, 1975 Italy .................................. 6606/75

[51] Int. Cl.² .......................................... G01N 15/04
[52] U.S. Cl. .................................... 73/61.4; 356/197
[58] Field of Search ........................ 73/61.4, 432 PS; 356/196, 197

[56] References Cited

U.S. PATENT DOCUMENTS

| 2,113,175 | 4/1938 | Elrod | 356/197 X |
| 3,009,388 | 11/1961 | Polanyi | 73/61.4 |
| 3,572,930 | 3/1971 | Morcom et al. | 73/61.4 X |
| 3,586,484 | 6/1971 | Anderson | 73/61.4 X |
| 3,652,860 | 3/1972 | Walker | 356/197 X |
| 3,679,367 | 7/1972 | Negersmith et al. | 73/61.4 X |
| 3,807,874 | 4/1974 | Gropper | 356/197 |

FOREIGN PATENT DOCUMENTS 24,847  9/1969  Japan ...................................... 73/61.4

Primary Examiner—Richard C. Queisser
Assistant Examiner—Joseph W. Roskos
Attorney, Agent, or Firm—Young & Thompson

[57] ABSTRACT

A centrifugal granulometer comprises a hollow circular horizontal plate that is driven in rotation about its vertical axis and that has a transparent peripheral zone. Particulate material is introduced into the interior of the plate at a predetermined distance radially inward of the periphery of the plate, where it becomes suspended in a liquid. Upon rotation of the plate, the particles migrate through the liquid radially outwardly in dependence on their mass and size. A light beam passing through the translucent peripheral portion is transmitted to a photoelectric receiver with an intensity that varies inversely as the concentration of particles in the peripheral zone. The plot of transmitted light versus time gives information as to the quantity and distribution of the particles according to size and weight.

7 Claims, 2 Drawing Figures

CENTRIFUGAL GRANULOMETER

The present invention relates to a centrifugal granulometer, comprising apparatus for determining by centrifugation the composition of pulverulent material according to the dimensions of the particles that constitute the material.

Such a granulometric determination permits one to classify the various particles according to their dimensions and to establish on the basis of a comparatively small quantity of material the relative proportions of the particles of various dimensions.

The apparatus in question is constituted by a rotor in the form of a hollow disc into which is introduced a sample of the particles whose granulometry is to be determined, at a predetermined distance radially inward of the periphery of the disc, where the particles become suspended in a liquid. The suspended sample is subjected to centrifugal force, whereupon the particles migrate radially outwardly through the liquid with a velocity that varies according to their mass and with a separation of the particles relative to each other according to their dimensions.

The coarser particles, therefore, followed by the finer particles, pass successively at various times through an annular translucent zone of the rotor, it being understood that the term "translucent" as used herein also includes transparent. A light beam directed through this translucent portion of the rotor is intercepted to a certain degree by the particles moving radially outwardly through the translucent zone.

The variation in the intensity of the light that is not intercepted by the particles, that is, that passes through the translucent zone despite the presence of suspended particles therein, registers on a photoelectric cell and can be recorded as a graph of transmitted light versus time. Such a graph gives useful information as to the size range of particles of the specimen and hence is useful in the granulometric analysis of specimen quantities of particulate material.

Figure 2:
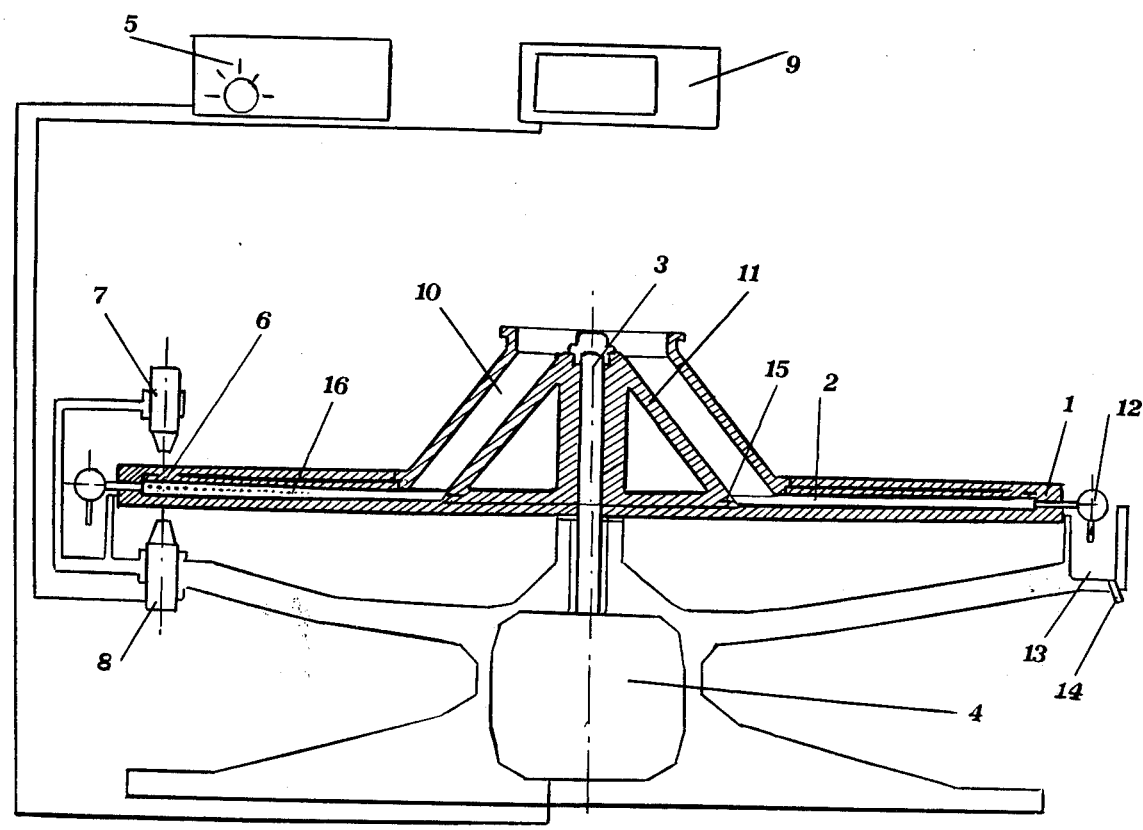

These and other features of the present invention will become apparent from a consideration of the following description, taken in connection with the accompanying drawing, in which:

FIG. 1 is a top plan view of the equipment according to the present invention; and FIG. 2 is a side elevational view which is partly in cross section on the line A—A of FIG. 1 and is somewhat schematic, of the apparatus according to the invention.

Referring now to the drawing in greater detail, there is shown apparatus according to the present invention, comprising a rotatable circular plate 1 provided with a flat annular internal chamber 2 and connected for rotation to a vertical axle 3 which is the output shaft of a drive motor 4. The plate, which serves as a centrifugal rotor, is driven in rotation by motor 4 under the control of a motor control 5 which regulates the speed of rotation of the motor and thus makes it possible to include another parameter or variable in the granulometric analysis of the specimen, namely, a variation in rotor velocity and hence centrifugal force, with time.

The rotor has a peripheral annular translucent zone 6 through which light rays pass which are emitted by a light source 7 parallel to the axis of rotation of plate 1 and which, having passed through the translucent zone 6 and a portion of the specimen undergoing granulometric analysis in suspension in a liquid, fall on the photoelectric cell 8. As indicated above, the quantity of light received by photocell 8 varies inversely as the quantity of suspended material in the specimen in translucent zone 6; and so the signal transmitted from photocell 8 to recorder 9 will vary in signal strength and, when plotted against time in a conventional manner, gives an indication of the granulometry of the specimen, the larger particles migrating faster under the influence of centrifugal force and the finer particles migrating slower. Recorder 9 can of course be of any conventional type that plots intensity of received electrical signal versus time.

In the upper central portion of the rotor is a frusto-conical feed passage providing an inlet 10 for the introduction of the specimen to the interior of the chamber 2. A frusto-conical body 11 is also secured concentrically to the axle 3 and insures that the test sample will all be disposed initially at a certain distance from the axis of rotation of the rotor and at a certain distance from the periphery of the rotor, thereby to insure that all of the suspended particles are subjected to substantially the same centrifugal forces and migrate substantially the same distance.

The hollow interior of the rotor may be emptied through two diametrically opposed valves 12 carried thereby, through conduits that communicate between the chamber 2 and an annular trough 13 from which the test specimen may be discharged through a conduit 14. Wash water can be introduced behind the specimen to promote the discharge of the specimen and the washing of the apparatus in preparation for the next specimen.

It is thus possible to perform rapidly and accurately a granulometric analysis of particulate material which is particularly improved with respect to known methods of granulometry that measure density, or levitation or sedimentation; and the present invention accordingly can have wide application in various fields, not only in industry but also in research.

By way of non-limitative example of the operation of the present invention, with reference to FIGS. 1 and 2, the various phases of a granulometric analysis using the apparatus of the invention will be set forth as follows:

1. With the valves 12 closed, the chamber 2 of the rotor 1 is filled with water or other dispersant liquid to the level 15 and the centrifuge is operated so as to register on the recorder 9 a linear graph that does not vary and hence serves as a reference line.

2. The finely divided specimen in dry or homogeneously suspended condition is introduced into the inlet 10 and the speed of rotation is adjusted by manipulation of control 5. The particles that arrive in the chamber 2 thus reach the liquid all at about the same radial distance from the axis of rotation of the dispersing liquid and so have all about the same length of path to travel, from the point where they enter the liquid to the point where they pass through the translucent zone 6. However, the particles traverse this distance with different velocities according to their mass and so fan out in a thin layer which progressively radially outwardly becomes thinner still as the periphery of the layer increases upon radial outward movement. The suspended particles thus dispose themselves in effect in concentric circular zones according to their dimensions, and so pass through the transparent zone 6 at different times and so intercept the passage of the light rays through the transparent zone 6 at different times and to a degree that depends on the quantity of the material in each of those concentric circular zones. The degree to which the light is intercepted by the suspended material is, as indicated above, detected by the photocell 8 and registered on the recorder 9.

3. When substantially all of the suspended material has traversed the translucent zone, and the graph again becomes linear as in the first or reference phase of the operation, the rotor can be suddenly braked, which agitates the liquid and the particulate material and so favors the discharge of the liquid with suspended particulate material when the valves 12 are opened. At the same time, wash water can be introduced into inlet 10 which washes out the chamber 2 in preparation for the next test.

4. There is thus produced by recorder 9 a graph which is a plot of the intensity of transmitted light, against time, and which accordingly is subject to interpretation as to granulometry of the test specimen in question.

It will of course be recognized that the form and construction and the dimensions of the apparatus according to the present invention may be varied as required by the uses to which it is to be put, without departing from the spirit of the present invention. Such modifications and variations are considered to be within the purview and scope of the present invention as defined by the appended claims.

What is claimed is:

1. A centrifugal granulometer comprising a centrifugal rotor in the form of a hollow disc, means mounting said disc for rotation about a vertical axis, means for rotating said disc about said vertical axis, a cone mounted for rotation coaxially with said disc, the base of the cone comprising the radially inner edge of a single flat continuous annular chamber within said disc, the disc having a single translucent continuous annular peripheral zone, means to project a light beam through said translucent zone, and photoelectric means to determine and record the intensity of said beam which has passed through said zone as a function of time, said cone comprising the inner wall of a frusto-conical feed passage for a specimen whose granulometry is to be determined, the lower edge of said feed passage opening into the inner edge of said annular chamber entirely about said inner edge.

2. A granulometer as claimed in claim 1, the path of said light beam being parallel to the axis of rotation of said disc.

3. A granulometer as claimed in claim 1, said rotating means comprising a motor, and means to vary the speed of rotation of said motor.

4. A granulometer as claimed in claim 1, said motor having a vertical drive shaft to which said disc and cone are concentrically secured.

5. A granulometer as claimed in claim 1, said means to project a light beam through said translucent zone and said photoelectric means being both fixed, with said disc rotating relative to them and between them.

6. A centrifugal granulometer comprising a centrifugal rotor in the form of a hollow disc, means mounting said disc for rotation about a vertical axis, means for rotating said disc about said vertical axis, a cone mounted for rotation coaxially with said disc, the base of the cone comprising the radially inner edge of a flat annular chamber within said disc, the disc having a translucent peripheral zone, means to project a light beam through said translucent zone, photoelectric means to determine and record the intensity of said beam which has passed through said zone as a function of time, and at least one valve at the periphery of the disc for the discharge of a specimen that has undergone analysis.

7. A granulometer as claimed in claim 6, there being a diametrically opposed pair of said valves on said disc.

* * * * *